United States Patent [19]

Suenaga et al.

[11] Patent Number: 5,312,958

[45] Date of Patent: May 17, 1994

[54] PROCESS FOR PRODUCING 4-BROMOMETHYLBIPHENYL COMPOUNDS

[75] Inventors: Syuji Suenaga, Oita; Hitoshi Kawaguchi, Fukuoka; Takeshi Kato, Osaka, all of Japan

[73] Assignee: Takeda Chemical Industries, Ltd., Osaka, Japan

[21] Appl. No.: 9,101

[22] Filed: Jan. 26, 1993

[30] Foreign Application Priority Data

Jan. 31, 1992 [JP] Japan .................. 4-046078
Nov. 9, 1992 [JP] Japan .................. 4-324831

[51] Int. Cl.$^5$ .................. C07C 253/30; C07C 255/50
[52] U.S. Cl. .................. 558/425; 548/250; 548/251; 560/102; 562/492; 564/161
[58] Field of Search .................. 558/425; 562/442; 560/102; 548/251; 564/161

[56] References Cited

FOREIGN PATENT DOCUMENTS 253310 1/1988 European Pat. Off. .
291969 11/1988 European Pat. Off. .
400974 12/1990 European Pat. Off. .
470794 2/1992 European Pat. Off. .

OTHER PUBLICATIONS

PCT 83/04021 (Patentbureau Danubia) dated Nov. 24, 1983.

*Primary Examiner*—Joseph Paul Brust
*Attorney, Agent, or Firm*—Wegner, Cantor, Mueller & Player

[57] ABSTRACT

A process for the production of a compound of general formula

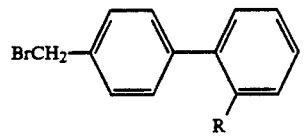

wherein R represents cyano, carboxy which may be esterified or amidated or tetrazolyl which may be substituted, comprising brominating the corresponding methyl compound with a brominating agent such as N-bromoacetamide, N-bromophtalimide, N-bromosuccinimide and so on in a halogenated hydrocarbon solvent in the presence of an azobis compound.

4 Claims, No Drawings

PROCESS FOR PRODUCING 4-BROMOMETHYLBIPHENYL COMPOUNDS

FIELD OF THE INVENTION

This invention relates to an industrially advantageous process for producing a class of 4-bromomethylbiphenyl compounds (hereinafter referred to as the compound (I)) which are of value as synthetic intermediates for the production of medicines, said compounds being represented by the following general formula

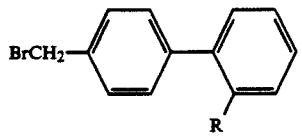

wherein R represents cyano, carboxy which may be esterified or amidated or tetrazolyl which may be substituted.

BACKGROUND OF THE INVENTION

A biphenylmethylimidazole compound having angiotensin II antagonizing activity and being of value as an antihypertensive drug or a therapeutic drug for congestive heart failure is disclosed in Japanese Patent Laid-open Publication No. 63-23868/1988, in which it is described that the compound (I), which is a synthetic intermediate, can be produced by brominating the corresponding 4-methylbiphenyl compound with N-bromosuccinimide in the presence of dibenzoyl peroxide in carbon tetrachloride at a temperature not exceeding the reflux temperature of the reaction system.

OBJECT OF THE INVENTION

However, the process involving the use of dibenzoyl peroxide, an explosive substance, is dangerous and not amenable to commercial production. Moreover, 90% of the reactor charge remains unconsumed at the completion of the reaction so that an alkaline substance must be used in substantial quantity for quenching. If savings be sought, actinic light irradiation is required but as is well known, such a procedure is unsuited for industrial scale production. Furthermore, since this reaction, which is exothermic, goes to completion within a brief time period of 15 to 20 minutes, it is a delicate task to control the heat of reaction. In addition, the yield is relatively modest, about 60%.

Therefore, development of a commercial process for producing compound (I) under mild conditions with safety and in good yield has been much awaited. The inventors of the present invention discovered that by brominating a 4-methylbiphenyl compound in the presence of an azobis compound in a halogenated hydrocarbon solvent, the corresponding compound of formula (I) can be produced in high yield under the mild conditions with safety. The present invention was developed on the basis of the above finding.

SUMMARY OF THE INVENTION

The present invention is directed to a process for producing a 4-bromomethylbiphenyl compound (I) characterized by brominating a 4-methylbiphenyl compound (hereinafter referred to as the compound (II)) of the general formula

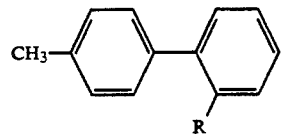

wherein R represents cyano, carboxy which may be esterified or amidated or tetrazolyl which may be substituted, in the presence of an azobis compound in a halogenated hydrocarbon solvent.

In the present specification, the substituent group on said tetrazolyl which may be substituted includes any of straight-chain or branched $C_{1-6}$ alkyl groups which may optionally be substituted by about 1 to 3 phenyl groups each, which phenyl groups may each be substituted by 1 to 3 substituent groups such as halogen, alkyl, alkoxy, hydroxy, nitro, etc.

The carboxy which may be esterified or amidated includes, among others, groups of the formula $-COOR^1$ and those of the formula $-CONR^2R^3$, wherein $R^1$, $R^2$ and $R^3$ independently represent hydrogen or a straight-chain or branched lower ($C_{1-6}$) alkyl group which may optionally be substituted with hydroxy group, amino group, halogen, a lower ($C_{1-4}$) alkoxy group or about 1 to 3 phenyl groups each, which phenyl groups may each be substituted by 1 to 3 substituent groups such as halogen, a lower ($C_{1-3}$) alkyl, a lower ($C_{1-4}$) alkoxy, hydroxy, nitro, etc.

As typical species of the compound (I) which can be produced by the process of the invention, there may be mentioned 4'-bromomethylbiphenyl-2-carbonitrile, 4'-bromomethylbiphenyl-2-carboxylic acid and its methyl, ethyl, isopropyl, tert-butyl, benzyl or p-nitrobenzyl esters, 4'-bromomethylbiphenyl-2-carboxamide and its N-methyl, ethyl, isopropyl, tert-butyl, benzyl or p-nitrobenzyl derivatives, N-triphenylmethyl-5-(4'-bromo-methylbiphenyl-2-yl)tetrazole, N-tert-butyl-5-(4'-bromomethylbiphenyl-2-yl) tetrazole and so on.

The brominating agent which can be used in the process of the present invention, among others, an organic compound containing bromine such as N-bromoacetamide, N-bromophthalimide, N-bromosuccinimide, N-bromomaleimide, N-bromosulfonamide and so on. Among them, the agent is preferably N-bromosuccinimide or N-bromophtalimide. The proportion of said agent is about 0.5 to 2 moles per mole of the starting compound (II).

The azobis compound which can be used in the present invention is represented by the general formula

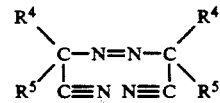

wherein $R^4$ and $R^5$ independently represent hydrogen or a straight-chain or branched lower ($C_{1-6}$) alkyl group optionally substituted with hydroxy group, amino group, imino group, halogen or a lower ($C_{1-4}$) alkoxy group; $R^4$ may be taken together with $R^5$ to form a ring, or their salts. The compound by the above formula includes, among others, 2,2'-azobisisobutyronitrile, 2,2'-azobis(2,4-dimethylvaleronitrile), 2,2'-azobis (2-methylbutyronitrile), azobisisovaleronitrile, 1,1'-azobis(cyclohexanecarbonitrile), 2,2'-azobis(4-methoxy -2,4- dimethylvaleronitrile), 2,2'-azobis(2-amidinopropane) hydrochloride, dimethyl 2,2'-azobisisobutyrate and so on. The preferred are azobisisonitriles, particularly 2,2'-azobisisobutyronitrile and 2,2'-azobis(2,4-dimethylvaleronitrile), and the most preferred is 2,2'-azobis (2,4-dimethylvaleronitrile). The proportion of said azobis compound is about 0.1 to 3% based on the brominating agent which is used in a proportion of about 0.5 to 2 moles per mole of starting compound (II). The preferred proportion is 2 to 3% for 2,2'-azobisisobutyronitrile and 0.1 to 0.3% for 2,2'-azobis (2,4-dimethylvaleronitrile). The halogenated hydrocarbon solvent which can be used includes methylene chloride, chloroform, dichloroethane, carbon tetrachloride, bromochlorethane, bromoethane etc., although methylene chloride is the most suitable.

The reaction, conducted at the reflux temperature of the system, goes to completion in about 30 minutes to 5 hours and stops spontaneously on discontinuation of refluxing. It should also be understood that depending on specific compounds, a prolonged reaction time exceeding 5 hours may result in liberation of bromine to give brown-colored crystals.

After completion of the reaction, the object compound can be isolated and purified by the conventional procedure such as recrystallization and chromatography.

By the process of the present invention, the object compound (I) can be produced under mild conditions, safely and in good yield. Compared with the reaction in carbon tetrachloride, the velocity of reaction in methylene chloride is so low that it is much easier to control the heat of reaction in a commercial plant. The compound (I) obtained in accordance with the invention can be used for example as a starting compound for the production of the angiotensin II antagonist described in Japanese Patent Laid-open Publication No. 63-23868/1988.

The following examples and comparative examples are merely intended to describe the present invention in further detail and should by no means be construed as defining the scope of the invention.

EXAMPLE 1

A four-necked glass flask equipped with a stirrer and reflux condenser was charged with 180 g of methylene chloride, 63.2 g of 4'-methylbiphenyl-2-carbonitrile, 58.8 g of N-bromosuccinimide and 90 mg of 2,2'-azobis (2,4-dimethylvaleronitrile) and the reaction was conducted under reflux with stirring at an internal temperature of 45°-47° C. for 3 hours. Refluxing was further continued for 1 hour and after cooling to an internal temperature of 35°-38° C., the reaction mixture was treated with 200 g of water twice to transfer the by-product succinimide into the water layer. The methylene chloride layer was allowed to cool gradually to 0° C., whereupon white crystals separated. The crystals were recovered by filtration, washed with cold methylene chloride and dried to give 71.6 g of 4'-bromomethylbiphenyl-2-carbonitrile. Yield 80.5%.

EXAMPLE 2

Using 900 mg of 2,2'-azobisisobutyronitrile instead of 2,2'-azobis(2,4-dimethylvaleronitrile), the reaction and workup procedure of Example 1 was otherwise repeated to give 70.5 g of 4'-bromomethylbiphenyl-2-carbonitrile as white crystals. Yield 79.2%

EXAMPLE 3

Using 69.4 g of 4'-methylbiphenyl-2-carboxylic acid instead of 4'-methylbiphenyl-2-carbonitrile, the reaction and workup procedure of Example 1 was otherwise repeated to give 76.6 g of 4'-bromomethylbiphenyl-2-carboxylic acid as white crystals. Yield 80.5 %.

EXAMPLE 4

Using carbon tetrachloride as the solvent, the reaction was conducted under reflux with stirring at an internal temperature of 77-78° C. for 1 hour in otherwise the same manner as Example 3. The reaction mixture was then worked up in the same manner as Example 1 to give 71.9 g of 4'-bromomethylbiphenyl-2-carboxylic acid as white crystals. Yield 75.5 %.

EXAMPLE 5

Using 69.1 g of 4'-methylbiphenyl-2-carboxamide instead of 4'-methylbiphenyl-2-carbonitrile, the reaction and workup procedure of Example 1 was otherwise repeated to give 57.4 g of 4'-bromomethylbiphenyl-2-carboxamide as white crystals. Yield 60.5 %.

EXAMPLE 6

A four-necked glass flask equipped with a stirrer and reflux condenser was charged with 15 g of methylene chloride, 3.0 g of N-triphenylmethyl-5-(4'-methylbiphenyl-2-yl)tetrazole, 1.13 g of N-bromosuccinimide and 1.7 mg of 2,2'-azobis(2,4-dimethylvaleronitrile) and the reaction was conducted under reflux with stirring at an internal temperature of 42° C. for 11.5 hours. (The reaction velocity was so low that about half the starting compound charge remained unreacted at 5 hours after initiation of reaction). After completion of the reaction, the reaction mixture was cooled to room temperature and phase separation with 15 ml of water was carried out twice. The solvent was then distilled off to give 3.51 g of a yellow solid. This solid was dissolved in 30 ml of the mixture solution of methylene chloride-ethyl acetate (1:1) and the solution was concentrated to about one-third of the initial volume. This concentrate was stirred under ice-cooling to cause precipitation of white crystals. These crystals were recovered by filtration, washed with 5 ml of ethyl acetate and dried to give 2.93 g (yield 83.8%) of N-triphenylmethyl-5-(4'-bromomethylbiphenyl-2-yl) tetrazole having the melting point of 137°-138° C. NMR δ (90MHz, CDCl$_3$): 4.37 (2H, s, CH$_2$), 6.83-8.20 (23H, m, Ar)

EXAMPLE 7

A four-necked glass flask equipped with a stirrer and reflux condenser was charged with 10 g of methylene chloride, 0.92 g of N-tert-butyl-5-(4'-methylbiphenyl-2-yl) tetrazole, 0.57 g of N-bromosuccinimide and 0.8 mg of 2,2'-azobis 2,4-dimethylvaleronitrile) and the reaction was conducted under reflux with stirring at an internal temperature of 42° C. for 23 hours. (The reaction proceeded slowly so that more than half the starting compound charge remained unreacted at 5 hours). After completion of the reaction, the reaction mixture was cooled to room temperature and phase separation with 20 ml of water was carried out twice. The solvent was then distilled off to obtain 1.49 g of an orange-colored solid. This solid was dissolved in 30 ml of the mixture solution of methylene chloride-ethyl acetate-hexane (1:1:1) and the solution was concentrated to about one-tenth of the initial volume. To the concentrate was added 1 ml of hexane and the mixture was stirred under ice-cooling to cause precipitation of light yellow crystals. The light yellow crystals were recovered by filtration, washed with 3 ml of ethyl acetate and dried to give 0.88 g (yield 75.3%) of N-tert-butyl-5-(4'-bromomethylbiphenyl-2-yl-)tetrazole having the melting point of 117.5°–118.5° C. NMR δ (90MHz, CDCl₃: 1.65 (9H, s, Me), 4.50 (2H, s, CH₂), 7.32–8.02 (8H, m, Ar)

EXAMPLE 8

Using carbon tetrachloride as the solvent, the reaction was conducted under reflux with stirring at an internal temperature of 80°–82° C. for 15 minutes in otherwise the same manner as Example 1. The reaction mixture was then worked up in the same manner as Example 1 to give white crystals of 4'-bromomethylbiphenyl-2-carbonitrile. Yield 75%

EXAMPLE 9

Using chloroform as the solvent, the reaction was conducted under reflux with stirring at an internal temperature of 64°–65° C. for 30 minutes in otherwise the same manner as Example 1 and the reaction mixture was worked up similarly to give 64.5 g of 4'-bromomethylbiphenyl-2-carbonitrile as white crystals. Yield 72.5%.

EXAMPLE 10

Using bromochloromethane as the solvent, the reaction was conducted under reflux with stirring at an internal temperature of 71°–74° C. for 50 minutes in otherwise the same manner as Example 1 and the reaction mixture was worked up similarly to give 62.7 g of 4'-bromomethylbiphenyl-2-carbonitrile as white crystals. Yield 70.5%.

EXAMPLE 11

Using bromoethane as the solvent, the reaction was conducted under reflux with stirring at an internal temperature of 41°–43° C. for 4 hours in otherwise the same manner as Example 1. The reaction mixture was then worked up in the same manner as Example 1 to give 67.2 g of 4'-bromomethylbiphenyl-2-carbonitrile as white crystals. Yield 70.2%.

EXAMPLE 12

Using N-bromoacetamide instead of N-bromosuccinimide as the brominating agent, the reaction and workup procedure of Example 1 was otherwise repeated to give 4'-bromomethylbiphenyl-2-carbonitrile as white crystals.

EXAMPLE 13

Using 76.2 g of N-bromophtalimide instead of N-bromosuccinimide as the brominating agent, the reaction was conducted under reflux with stirring in otherwise the same manner as Example 1 and after cooling to an internal temperature of 35°–38° C., the reaction mixture was treated with 200 g of 0.2% sodium hydroxide solution twice to transfer the byproduct phtalimide into the water layer. Then, by the same treatment as Example 1, 66.4 g of 4'-bromomethylbiphenyl-2-carbonitrile was obtained as white crystals. Yield 79.6%.

EXAMPLE 14

Using carbon tetrachloride as the solvent and 76.2 g of N-bromophtalimide instead of N-bromosuccinimide as the brominating agent, the reaction was conducted under reflux with stirring at an internal temperature of 77°–78° C. for 1 hour in otherwise the same manner as Example 1. The reaction mixture was then worked up in the same manner as Example 13 to give 63.6 g of 4'-bromomethylbiphenyl-2-carbonitrile as white crystals. Yield 71.5%.

COMPARATIVE EXAMPLE 1

Using 2.8 g (corresponding to twice the amount used in Japanese Patent Laid-open Publication No. 63-23868/1988) of dibenzoyl peroxide instead of 2,2'-azobis (2,4-dimethylvaleronitrile), the reaction was conducted in carbon tetrachloride under reflux at an internal temperature of 80°–82° C. The reaction went to completion in 15 minutes. The reaction mixture was then worked up in the same manner to give 58.9 g of 4'-bromomethylbiphenyl-2-carbonitrile as white crystals. Yield 65.5%

COMPARATIVE EXAMPLE 2

Using dibenzoyl peroxide in an amount of 378 mg and performing an irradiation with infrared light in combination, the reaction was conducted in otherwise the same manner as Comparative Example 1. The reaction went to completion in 20 minutes. The reaction mixture was then worked up in the same manner to give 57.9g of 4'-bromomethylbiphenyl-2-carbonitrile as white crystals. Yield 65.1%. Incidentally, the reaction did not proceed when infrared irradiation was not performed.

The following references, which are referred to for their disclosure at various points in this application, are incorporated herein by reference.

Japanese Patent Laid-open Publication No. 63-23868/1988.

What is claimed is:

1. A process for producing a 4-bromomethylbiphenyl compound of the formula:

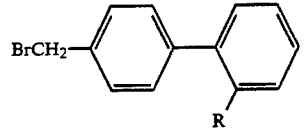

wherein R represents cyano, carboxy, carbamoyl or tetrazolyl which may be substituted with a straight-chain or branched C₁₋₆ alkyl group which may be substituted with 1 to 3 phenyl groups, which comprises brominating a compound of the formula:

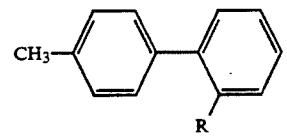

Wherein R is as defined above, with a brominating agent selected from the group consisting of N-bromoacetamide, N-bromophthalimide, N-bromosuccinimide, N-bromomaleimide and N-bromosulfonamide, in the presence of an azobis compound represented by the formula:

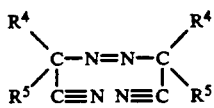

, wherein $R^4$ and $R^5$ independently represent hydrogen or a straight-chain or branched lower $C_{1-6}$ alkyl group optionally substituted with hydroxy, amino, imino, halogen or a lower $C_{1-4}$ alkoxy group; $R^4$ may be taken together with $R^5$ to form a ring, in a methylene chloride solvent.

2. A process according to claim 1, wherein N-bromosuccinimide or N-bromophtalimide is used as the brominating agent.

3. A process according to claim 1, wherein the azobis compound is 2,2'-azobis(2,4-dimethylvaleronitrile).

4. A process according to claim 1, wherein R is cyano.

* * * * *